United States Patent [19]
Johansson et al.

[11] Patent Number: 5,792,129
[45] Date of Patent: Aug. 11, 1998

[54] SANITARY NAPKIN

[75] Inventors: Kerstin Johansson, Ulricehamn; Roy Hansson, Mölndal, both of Sweden

[73] Assignee: Mölnlycke AB, Göteborg, Sweden

[21] Appl. No.: 604,974

[22] PCT Filed: Oct. 6, 1994

[86] PCT No.: PCT/SE94/00933

§ 371 Date: Mar. 20, 1996

§ 102(e) Date: Mar. 20, 1996

[87] PCT Pub. No.: WO95/09592

PCT Pub. Date: Apr. 13, 1995

[30] Foreign Application Priority Data

Oct. 7, 1993 [SE] Sweden ................... 9303284

[51] Int. Cl.⁶ .......................................... A61F 13/15
[52] U.S. Cl. ....................... 604/387; 604/378; 604/385.1
[58] Field of Search ......................... 604/367, 308, 604/385.1, 387, 378, 388–396

[56] References Cited

U.S. PATENT DOCUMENTS

| | | | |
|---|---|---|---|
| 3,463,154 | 8/1969 | Hendricks | 604/387 |
| 4,333,466 | 6/1982 | Matthews | 604/387 |
| 4,758,241 | 7/1988 | Papjohn | 604/387 |
| 4,940,462 | 7/1990 | Salerno | 604/387 |
| 5,275,591 | 1/1994 | Mavinkurve | 604/385.1 |

FOREIGN PATENT DOCUMENTS

| | | |
|---|---|---|
| 391 727A2 | 10/1990 | European Pat. Off. . |
| 3600420 A1 | 7/1986 | Germany . |
| 433156 | 9/1967 | Switzerland . |
| 295799 | 8/1928 | United Kingdom . |
| 2087731 | 6/1982 | United Kingdom . |
| 2144995 | 3/1985 | United Kingdom . |
| 2170108 | 7/1986 | United Kingdom . |
| 2175212 | 11/1986 | United Kingdom . |
| 2198357 | 6/1988 | United Kingdom . |
| 2215609 | 9/1989 | United Kingdom . |
| 2266464 | 11/1993 | United Kingdom . |
| WO 91/11165 | 8/1991 | WIPO . |

*Primary Examiner*—Robert A. Clarke
*Attorney, Agent, or Firm*—Burns, Doane, Swecker & Mathis, L.L.P.

[57] ABSTRACT

The present invention relates to a sanitary napkin or like absorbent article, such as a sanitary pantie or incontinence guard, comprising an absorbent body (8) which is enclosed between a fluid-permeable (15) and a fluid-impermeable casing sheet (17). According to the invention, the absorbent body (8) comprises a primary absorbent body (9) having the capacity to absorb all fluid discharged from a user over an intended article use period, and a secondary absorbent body (10) whose area is at least 50% larger than the area of the primary absorbent body.

11 Claims, 3 Drawing Sheets

SANITARY NAPKIN

BACKGROUND OF THE INVENTION

1. Field of the Invention

The present invention relates to a sanitary napkin or like absorbent article, such as a pantie or incontinence guard, comprising an absorbent body which is enclosed between a fluid-permeable and a fluid-impermeable casing sheet.

2. Description of Related Art

Despite present-day sanitary napkins having absorbent bodies which, almost without exception, have an absorbency which is far greater than what is required to absorb the total amount of fluid discharged during the period over which the napkin is worn, leakage of fluid from the napkin is not an unusual occurrence. Leakage can be caused by the napkin being deformed or moved from its effective position as a result of the movements of the wearer, or because the napkin has been wrongly positioned in the pantie from the outset. A particular problem in this connection is found in those deformations that occur during the night, due to the recumbent position of a sleeping wearer, which will often result in rearward leakage with subsequent soiling of the wearer's night linen and bed linen.

OBJECTS AND SUMMARY

A primary object of the present invention is to solve this problem and to provide a sanitary napkin or like article with improved leakage safety.

This object is achieved in accordance with the invention with a sanitary napkin of the kind defined in the introduction which is characterized in that the absorbent body includes a primary absorbent body having the capacity to absorb all fluid discharged by a user during the intended use period of the article, and a secondary absorbent body which has an area which is at least 50% larger than the area of the primary absorbent body. This provision of the secondary absorbent body eliminates practically all risk of fluid leaking from the napkin.

According to one preferred embodiment of the invention, the area of the secondary absorbent body is at least 70% larger than the area of the primary absorbent body and the secondary body is more flexible or pliable than the primary body. The secondary absorbent body also extends beyond the primary absorbent body around the full circumference thereof, and the primary absorbent body is placed in the front part of the secondary absorbent body, as seen in the use position of the napkin, and when the sanitary napkin is worn lies proximal to the wearer's body in that part of the sanitary napkin where the primary and the secondary absorbent body mutually overlap. The secondary absorbent body comprises advantageously one or more tissue layers and is provided with means which counteract fluid transport in the absorbent material. These fluid transport counteracting means consist of folds formed in the secondary absorbent body or of lines or regions of non-absorbent material formed in the secondary absorbent body. According to one variant, the fluid transport counteracting means are absorbent fibers capable of binding absorbed fluid chemically.

The inventive sanitary napkin is intended for coaction with a pantie that includes a front-part, a back-part and an intermediate crotch-part, and at least that part of the secondary absorbent body which is intended to be placed in the central part of the crotch-part of the pantie has the same shape as said central part.

BRIEF DESCRIPTION OF THE DRAWINGS

An inventive sanitary napkin will now be described in more detail with reference to the accompanying drawings, in which.

DETAILED DESCRIPTION OF PREFERRED EMBODIMENTS

Figure 1:
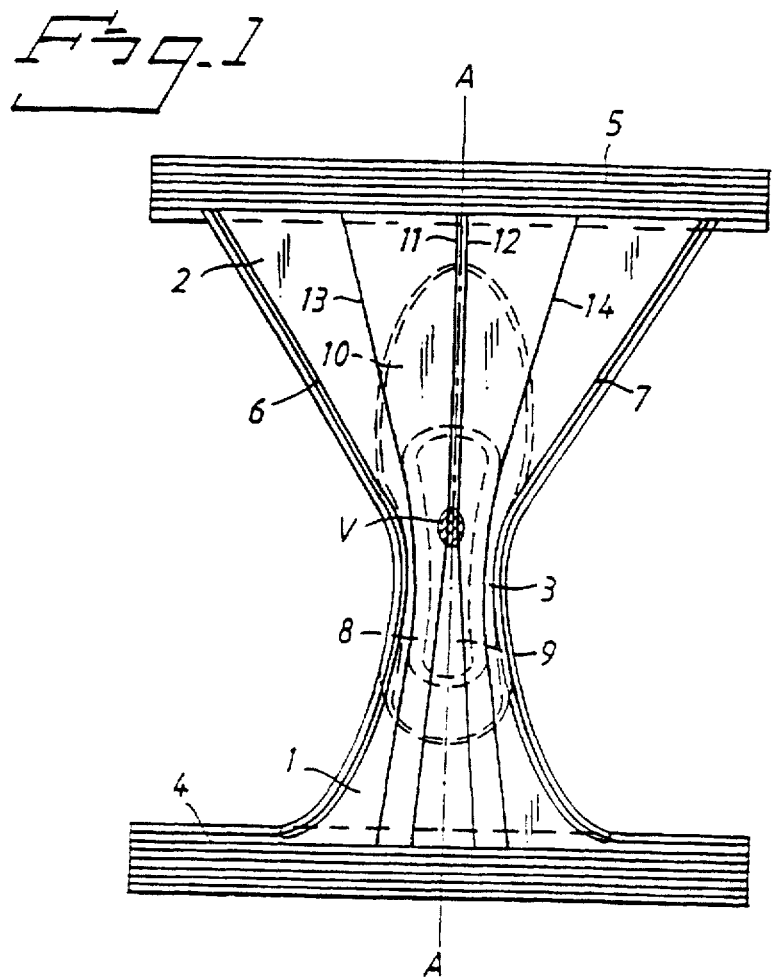
FIG. 1 illustrates one embodiment of an inventive sanitary napkin inserted into a pantie.

FIG. 1 illustrates a stage in the manufacture of a sanitary pantie according to one embodiment of the invention and shows the pantie in a stage of manufacture prior to joining together the front and the rear waist-parts. The illustrated pantie includes a front-part 1, a back-part 2 and an intermediate crotch-part 3. The pantie is also provided conventionally with waist elastic, which in the illustrated case has the form of elastic ribbon 4, 5 mounted along the front-part and the back-part of the waist edge, and leg elastic in the form of elastic threads 6, 7 extending along the side-contours of the pantie between the elastic ribbons 4, 5. In the illustrated case, two elastic threads are mounted along each side-edge of the pantie, although it will be understood that the leg elastic may, instead, consist of more or fewer threads than shown or of elastic ribbons or the like. FIG. 1 also shows an absorbent body or pad 8 in broken lines, which may be either attached firmly to the pantie or removably joined thereto. The illustrated absorbent body 8 is comprised of a primary absorbent body 9 and a secondary absorbent body 10 and is particularly suited for night use.

The pantie is also provided with two elastic threads 11, 12 which extend between the respective elastic ribbons 4 and 5 of the front and back parts 1, 2, symmetrically in relation to a centre line A—A extending in the longitudinal direction of the pantie. The threads 11, 12 extend close together and parallel with the longitudinal pantie line, from the waist-edge of the back-part 2 or the rear-edge of said back-part to a crotch region V, which when the pantie is worn is located in the midriff region of the wearer. The threads 11, 12 extend divergently from this region V to the waist-edge or the front-edge of the front-part of the pantie.

Figure 4:
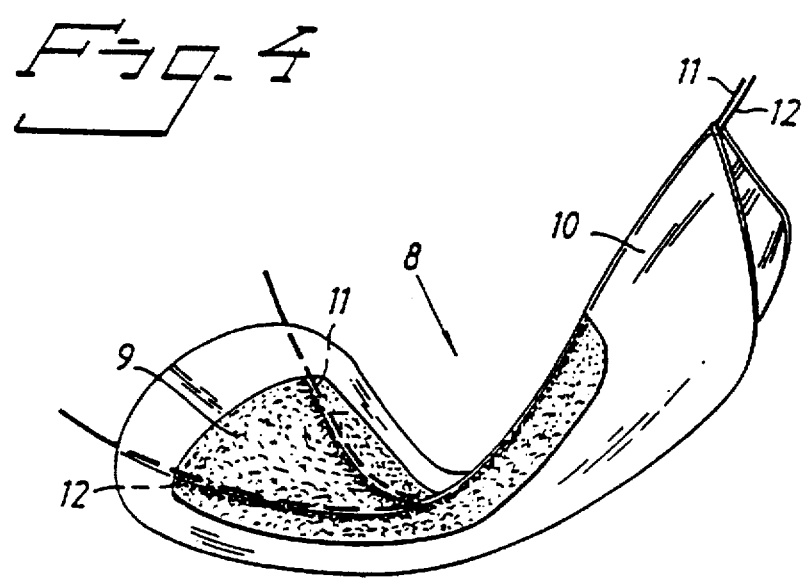
FIG. 4 illustrates schematically deformation of an absorbent body inserted in a pantie according to FIGS. 1–3 when worn.

When wearing a pantie constructed in accordance with the FIG. 1 embodiment, those parts of the threads 11, 12 which diverge forwardly from the region V strive to bring the absorbent body 8 to a basin-like shape within this region, this basin-like shape corresponding well to the wearer's anatomy within this region. Those mutually parallel parts of the threads 11, 12 which extend rearwardly from the region V strive to press corresponding central parts of the absorbent body 8 in between the wearer's buttocks when the pantie is worn, thereby causing the absorbent body to lie safely against the wearer's body, at least within the crotch-part and the beginning of the back-part of the pantie, so as to provide effective safety against rearward leakage. The aforementioned shaping of the absorbent body is illustrated schematically in FIG. 4.

The pantie illustrated in FIG. 1 also includes elastic threads 13, 14 which lie laterally outside the threads 11, 12 and which are mutually convergent between the front-part and the back-part of the pantie and are mutually divergent in the back part of the pantie. The elastic threads 13, 14 follow the side contours of the primary absorbent body 9, along a major part of their length extension. The threads 13, 14 thus ensure that the side-edges of the primary absorbent body will be pressed into sealing abutment with the wearer's body and also contribute towards ensuring that the secondary absorbent body will follow the wearer's body effectively. It should be mentioned in this connection that the secondary absorbent body is thin and very pliable and is intended to form an additional safety zone for absorbing any leakage that may occur during long-term use of the absorbent body, for instance over a full night, and that its absorption capacity may be relatively small.

When the absorbent body that coacts with the sanitary pantie is to form an integral part of the pantie, the absorbent body is preferably anchored to the pantie in the stage of manufacture illustrated in FIG. 1, in which the aforedescribed elastic elements are in a stretched state. When manufacture of the pantie is completed, the elastic elements strive to contract to a relaxed or tensionless state. This results in the formation of folds in those regions of the pantie which lie outside the primary absorbent body 9, and the threads will contract to a generally relaxed state within these regions. Within the region of the primary absorbent body 9, the absorbent body counteracts gathering of the pantie into folds, to a greater or lesser extent dependent on the stiffness thereof. Present-day thin absorbent bodies are extremely pliable and will therefore be folded by the elastic threads, although the threads are prevented from relaxing totally. Thus, when the pantie is put on the wearer's body, the folds in the absorbent body 9 will be smoothed out and the body will be brought into abutment with the wearer's body by the elastic force in respective threads 11–14. The absorbent body 9 will obtain a concave basin-like shape from the region V and forwards, due to the wearer's anatomy, causing the contracting force exerted by the threads 11–14 within this region to strive to retain this basin-like shape while, at the same time, those parts of the absorbent body 9 which lie along the threads will be pressed into sealing abutment with the wearer's body. The mutually parallel parts of the threads 11, 12 ensure that the part of the absorbent body 9 that lies rearwards of the region V will be deformed so as to conform to the shape of the wearer's anatomy in this region and so that the part of the absorbent body that lies between the wearer's buttocks will come into sealing abutment with the wearer's body. In addition to ensuring that the side-edges of the absorbent body 9 will sealingly abut the wearer's body, the elastic threads 13, 14 also function to prevent the formation of folds or buckles in the pantie or in the secondary absorbent body.

When the pantie illustrated in FIG. 1 is intended to be used together with a removable absorbent body, the absorbent body should be inserted with the elastic threads outwardly stretched at least within the region of attachment of the primary absorbent body. A pantie of this kind will function essentially in the manner described above with reference to an integrated absorbent body. This is also a natural method of attaching the absorbent body, since folds would otherwise form in the crotch-part of the pantie. It should be mentioned in this connection that a removable absorbent body which is intended to coact with the inventive pantie will preferably have a stiffness such as not to be folded by the elastic threads after attachment to the pantie, but merely curved.

Figure 2:
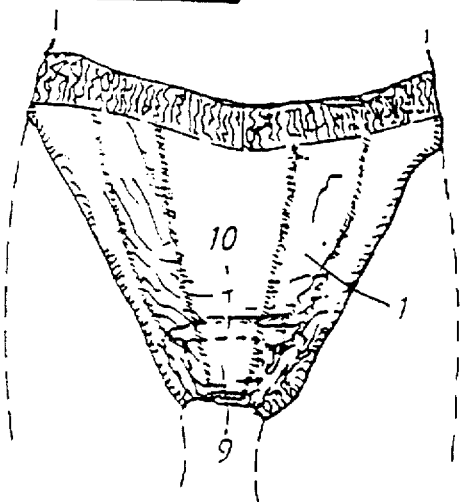
FIG. 2 is a front view of the sanitary pantie of FIG. 1 and shows the pantie assembled and worn.
Figure 3:
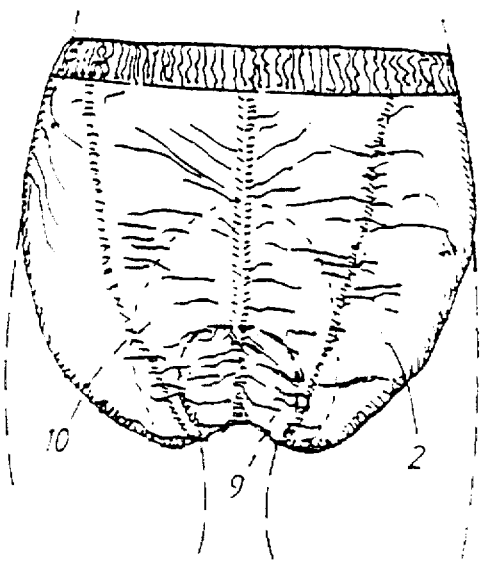
FIG. 3 is a rear view of the sanitary pantie of FIG. 1 and shows the pantie assembled and worn.

FIGS. 2 and 3 illustrate schematically the form taken by the sanitary pantie of FIG. 1 when worn, the relevant parts of the wearer's body being shown in broken lines.

In the case of the FIG. 1 embodiment, the elastic devices 11–14 are elastic threads. It will be understood, however, that the necessary elasticity of the pantie can be achieved in ways other than with the aid of elastic threads. For instance, the elastic devices may have the form of elastic bands, ribbons or elastic film, or nonwoven material cut to the desired shape. It is also conceivable to produce the pantie from an elastic material and to remove the elastic properties of the material in some suitable way within desired regions or areas. Different types of elastic material may be combined in the illustrated pantie. For instance, soft bands or ribbons of elastic foam may be used as leg elastic, while complete pieces of elastic nonwoven material may be used for the waist elastic. It is also conceivable for the elastic devices 11–14 to comprise parts of mutually different materials. For instance, the parallel parts of the threads 11, 12 can be replaced with a centrally extending band while the diverging parts are comprised of elastic threads.

The pantie illustrated in FIG. 1 is preferably comprised of two sheets which are mutually joined in some appropriate manner, for instance glued, and the elastic devices are mounted between these sheets and fastened thereto, for instance glued or welded with ultrasonic welds or heat welds. The elastic may also be sewn in the pantie.

As before mentioned, the absorbent body 8 illustrated in FIG. 1 is comprised of a primary and a secondary absorbent body 9 and 10 respectively. The primary absorbent body 9 is constructed in the same manner as a conventional absorbent body or pad of a sanitary napkin and will have an absorbency sufficient to handle fluid discharged by the wearer over the intended use time-period, for instance a full night. For instance, the absorbent body may be comprised of one or more layers of compressed cellulose fluff which may or may not contain superabsorbent material, said fluff pulp preferably having been earlier air-laid and treated so as to form a web that can be rolled onto reels, or of one or more layers of other roll material. The primary absorbent body could also comprise a material sheet containing so-called superabsorbent material and a material sheet without superabsorbent material.

The secondary absorbent body 10 has a much greater extension than the primary absorbent body and extends rearwardly over a large part of the back-part of the pantie. The primary object of the secondary absorbent body 10 is to improve leakage safety and to this end the secondary body shall have an area which is at least 50%, preferably at least 70%, larger than the area of the primary absorbent body and shall have a given absorption capacity. The secondary absorbent body may be comprised of tissue or nonwoven roll-material of different kinds. The secondary absorbent body 10 will preferably also include means for preventing fluid from spreading across its surface. Such fluid-spreading barriers may be obtained by folding, pleating or crêping the material layers or by providing barrier-forming welds. Another way of achieving a fluid-barrier effect is to form in the absorbent material of the secondary absorbent body compression lines which control fluid dispersion and therewith counteract dispersion or spreading of fluid in a direction perpendicular to such a line. It is also conceivable to use a nonwoven material which includes fibers of so-called superabsorbent material which when absorbing fluid bind the absorbed fluid chemically. However, the secondary absorbent body must, in the main, be equally as supple or pliable as the pantie material, so that the pantie can be worn comfortably.

The secondary absorbent body must therefore be made very thin and will subsequently have a highly limited absorbency.

As will be seen from FIG. 1, the side-contours of the secondary absorbent body follow the side-contours of the pantie within the region of the narrowest part of the crotch-part. This is highly advantageous when the combined absorbent body 8 is a removable type body, since its configuration clearly indicates where the absorbent body 8 shall be placed in the pantie. This eliminates to a large extent the risk of a user placing the absorbent body wrongly in the pantie.

Figure 5:
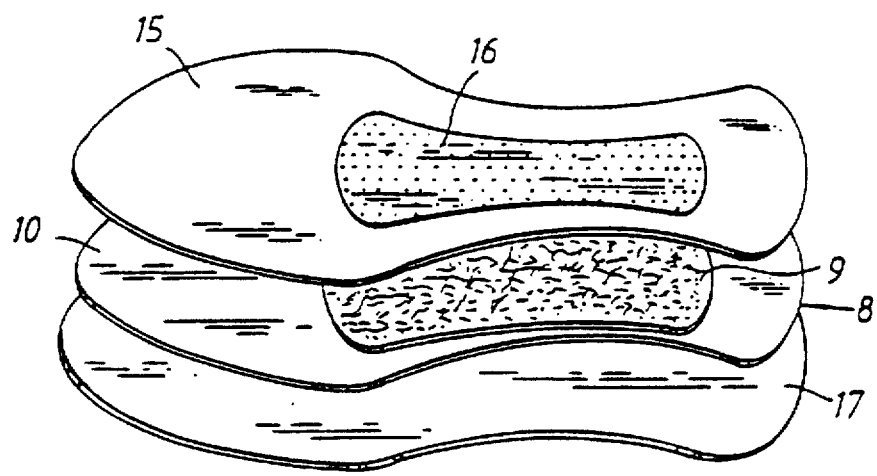
FIG. 5 is an exploded view of the sanitary napkin shown in FIG. 1.

FIG. 5 is a schematic exploded view of one embodiment of an inventive sanitary napkin, which comprises conventionally an absorbent body 8 enclosed between a fluid-permeable and a fluid-impermeable casing sheet 15 and 17 respectively.

The fluid-permeable casing sheet 15 is preferably comprised of nonwoven material, although other types of fluid-permeable materials traditionally used as outer materials in absorbent articles, such as sanitary napkins, diapers, incontinence guards or the like, for instance perforated plastic sheet, may also be used of course. In the illustrated variant, that part of the fluid-permeable casing sheet 15 which lies over the primary absorbent body is comprised of a perforated plastic sheet 16 of the type which will give the feeling of a dry surface in direct contact with the skin, whereas the remainder of the fluid-permeable casing sheet may be comprised of nonwoven material.

The fluid-impermeable casing sheet 17 is intended to prevent fluid penetrating to the pantie and may be comprised of plastic sheet, hydrophobic non-woven material or may be part of a plastic and non-woven laminate structure. This sheet, however, will preferably be air-permeable, at least within the region of solely the second absorbent body, since a pantie that carries a sanitary napkin will otherwise become warm when worn.

When the sanitary napkin forms an integral part of a sanitary pantie and forms together therewith a so-called trouser-like sanitary napkin, the fluid-permeable casing sheet 15 may be included in the inner sheet of a two-sheet pantie.

Figure 6:
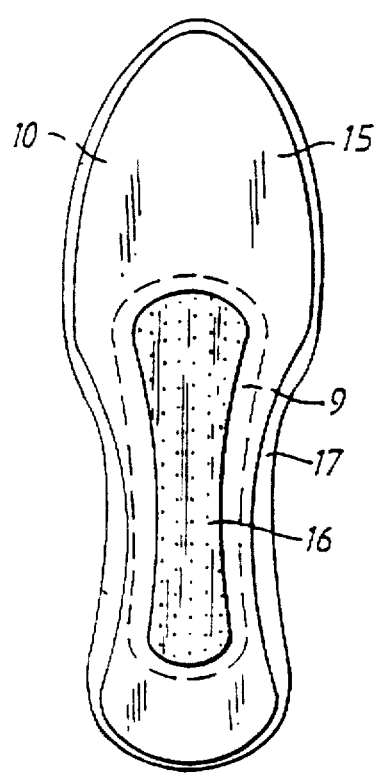
FIG. 6 illustrates the sanitary napkin of FIG. 2 from above.
Figure 7:
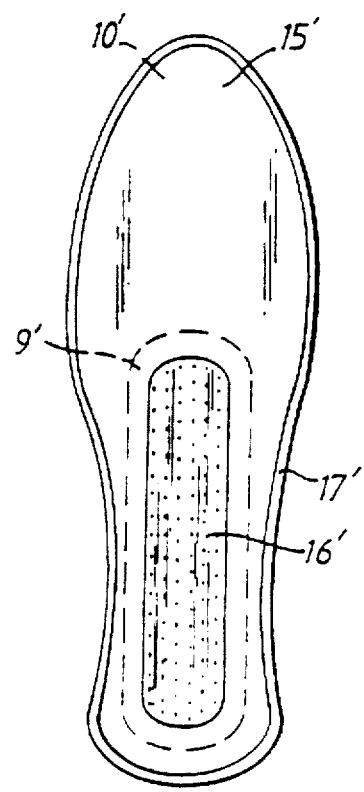
FIG. 7 illustrates a variant of the napkin shown in FIGS. 1–3.

FIG. 7 illustrates a variant of the sanitary napkin shown in FIG. 6. The sole difference between the FIG. 7 and FIG. 6 embodiments is that the primary absorbent body of the FIG. 7 embodiment has a slightly different shape and is placed somewhat differently in relation to the primary absorbent body of the FIG. 6 embodiment. Those components of the FIG. 7 embodiment which find correspondence in the FIG. 6 embodiment have been identified with the same reference signs to which a prime has been added.

The described sanitary napkin is intended primarily for night use and for use together with a pantie constructed in accordance with FIG. 1, and provides particularly good safety against leakage. It will be understood, however, that the described sanitary napkin can be used with conventional panties and still be extremely safe against leakage, particularly when it is ensured that the secondary absorbent body extends beyond the point at which the wearer's buttocks meet in an upward direction. In addition to a higher degree of leakage safety, the invention also enables the primary absorbent body to be dimensioned optimally, since the absorbent body need not be constructed to provide safety against leakage on its own. Consequently, the invention enables the primary absorbent body to be made smaller than would otherwise be the case, resulting in more effective use of its absorbent material.

It will also be understood that the described and illustrated embodiments of the sanitary napkin can be modified within the scope of the invention, particularly with respect to the shape of the secondary absorbent body. For instance, the rearwardly extending part of the secondary absorbent body may be straight instead of having the curved sides illustrated in the drawings. The invention is therefore limited solely by the content of the following claims.

We claim:

1. An absorbent article such as a sanitary napkin, a sanitary pantie or an incontinence guard, comprising an absorbent body, the absorbent body being enclosed between a fluid-permeable casing sheet and a fluid-impermeable casing sheet and having a forward part and a rear part, the absorbent body including a primary absorbent body and a secondary absorbent body, the secondary absorbent body has an absorption capacity which is lower than an absorption capacity of the primary absorbent body, an area of the secondary absorbent body is at least 50% larger than an area of the primary absorbent body, the secondary absorbent body including an area extending beyond a full circumference of the primary absorbent body, and the extending area of said secondary absorbent body being greatest at the rear part of the absorbent body.

2. The absorbent article according to claim 1, whereby the area of the secondary absorbent body is at least 70% larger than the area of the primary absorbent body.

3. The absorbent article according to claim 2, whereby the secondary absorbent body is more flexible than the primary absorbent body.

4. The absorbent article according to claim 1, whereby the secondary absorbent body is more flexible than the primary absorbent body.

5. An absorbent article according to claim 1, wherein the secondary absorbent body is comprised of one or more tissue layers.

6. An absorbent article according to claim 1, wherein the secondary absorbent body is comprised of nonwoven material.

7. An absorbent article according to claim 1, wherein the secondary absorbent body is provided with means for counteracting fluid transport in the absorbent material.

8. An absorbent article according to claim 7, wherein the fluid transport counteracting means are folds formed in the secondary absorbent body.

9. An absorbent article according to claim 7, wherein the fluid transport counteracting means are comprised of lines of non-absorbent material formed in the secondary absorbent body.

10. An absorbent article according to claim 7, wherein the fluid transport counteracting means are comprised of absorbent fibres capable of chemically binding absorbed fluid.

11. An absorbent article according to claim 1 intended for coaction with a pantie that comprises a front-part, a back-part and a central part, wherein at least a part of the secondary absorbent body that is intended to be placed in the central part of the pantie has a same shape as said central part.

* * * * *